(12) United States Patent
Fontana et al.

(10) Patent No.: US 8,863,762 B2
(45) Date of Patent: Oct. 21, 2014

(54) ELASTOMERIC DENTAL FLOSS

(75) Inventors: José Eder Fontana, São Paulo (BR);
Edilberto Lemos, Santo André (BR);
Fernando Perna, São Paulo (BR); Paulo Focassio, São Paulo (BR)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/508,050

(22) PCT Filed: Nov. 5, 2010

(86) PCT No.: PCT/US2010/055656
§ 371 (c)(1),
(2), (4) Date: May 4, 2012

(87) PCT Pub. No.: WO2011/057095
PCT Pub. Date: May 12, 2011

(65) Prior Publication Data
US 2012/0222698 A1  Sep. 6, 2012

Related U.S. Application Data

(60) Provisional application No. 61/258,411, filed on Nov. 5, 2009.

(51) Int. Cl.
| A61C 15/00 | (2006.01) |
| A61C 15/04 | (2006.01) |
| D01F 6/46 | (2006.01) |
| D01F 6/56 | (2006.01) |

(52) U.S. Cl.
CPC ............... *A61C 15/041* (2013.01); *D01F 6/46* (2013.01); *D01F 6/56* (2013.01)
USPC .......................................................... 132/321

(58) Field of Classification Search
USPC .................. 132/321–329; 424/424
See application file for complete search history.

(56) References Cited

U.S. PATENT DOCUMENTS

| 3,511,249 | A | 5/1970 | Baitz |
| 5,076,300 | A | 12/1991 | Mayfield |
| 5,334,646 | A | 8/1994 | Chen |
| 5,508,334 | A | 4/1996 | Chen |
| 5,755,243 | A | 5/1998 | Roberts et al. |
| 5,875,797 | A | 3/1999 | Chiang et al. |
| 5,918,609 | A | 7/1999 | Tsao et al. |
| 5,941,256 | A | 8/1999 | Guay et al. |
| 5,962,572 | A | 10/1999 | Chen |
| 6,029,678 | A | 2/2000 | Tsao et al. |
| 6,123,982 | A | 9/2000 | Fontana |
| 6,161,555 | A | 12/2000 | Chen |
| 6,289,904 | B1 | 9/2001 | Suhonen et al. |
| 6,333,374 | B1 | 12/2001 | Chen |
| 6,340,027 | B1 | 1/2002 | Hagne et al. |
| 6,552,109 | B1 | 4/2003 | Chen |
| 6,627,275 | B1 | 9/2003 | Chen |
| 6,867,253 | B1 | 3/2005 | Chen |
| 7,222,380 | B2 | 5/2007 | Chen |
| 7,290,367 | B2 | 11/2007 | Chen |
| 2003/0083422 | A1 | 5/2003 | Chen |
| 2004/0123877 | A1 | 7/2004 | Brown et al. |
| 2006/0207628 | A1 | 9/2006 | Millis |
| 2007/0197949 | A1* | 8/2007 | Chen .............................. 602/41 |

FOREIGN PATENT DOCUMENTS

WO   WO 2011/057095   5/2011

OTHER PUBLICATIONS

ISR and Written Opinion for PCT/US2010/055656 mailed on Mar. 3, 2011.
ISR and Written Opinion for PCT/US2010/055667 mailed on Aug. 1, 2011.
Product Information on "GUM® Expanding Floss", 2009.

* cited by examiner

*Primary Examiner* — Rachel Steitz
(74) *Attorney, Agent, or Firm* — Anne Louise St. Martin

(57) ABSTRACT

A composition comprising a melted blend of polypropylene and an elastomeric block copolymer, and a plasticizer useful as an oral cleaning device. The elastomeric composition may be used as a dental floss.

10 Claims, No Drawings

ELASTOMERIC DENTAL FLOSS

CROSS REFERENCE TO RELATED APPLICATIONS

This application is a national stage entry under 35 U.S.C. §371 of International Patent Application No. PCT/US2010/055656, filed 5 Nov. 2010, which claims priority to U.S. Provisional Patent Application Ser. No. 61/258,411, filed on Nov. 5, 2009, which is incorporated herein by reference.

BACKGROUND

The use of dental floss and other interdental cleaners are an important part of dental hygiene, and are used to remove plaque and other particulate from between the teeth and under the gum line, e.g., areas in the mouth where a toothbrush cannot reach. Frequently, these are the initiation sites of tooth decay, especially if not cleaned regularly. However, even with routine maintenance, caries and gingivitis still develop in these areas. Thus, there is a continuing need to develop more effective dental flosses.

Dental flosses are generally linear strips of a material having a fixed diameter/dimensions. However, teeth are not all equally spaced apart. Thus, use of a dental floss that has a diameter less than the distance between the teeth results in inefficient or ineffective cleaning between the teeth. In addition, a space usually resides between the gum and two adjacent teeth that is usually larger than the diameter of dental floss, and efficient cleaning of such area is difficult. Dental floss users occasionally use dental floss to massage the gums, but dental flosses generally are hard when pulled taut, resulting in potential damage to the gum.

Solutions to overcome such problems include manufacturing dental flosses having a wider diameter. This may pose problems insofar as it may be difficult to pass larger diameter flosses, or even normal diameter flosses, between the teeth without a substantial increase of force. The force exerted to pass the floss between the teeth is immediately released once the floss passes between the teeth, usually resulting in a painful collision with the gums, and resulting in possible lacerations and bleeding. Also this "extra" force exerted to pass the floss between the teeth would cause a fiber filaments rupture provoking shred and fray. Thus, small children may even be discouraged from flossing due to possible self-inflicted injuries.

Gelatinous elastomeric articles are known in the art, and often are used as handles for umbrellas, brushes, or for toys, dental floss, hand exercising grips, cushions, and the like. U.S. Pat. Nos. 5,334,646, and 5,508,334, the disclosures of which are incorporated by reference herein in their entirety, discloses a gelatinous composition comprised of an intimate blend admixture of poly(styrene-ethylene-butylene-styrene) triblock copolymer with a high level of a plasticizing oil. These gelatinous polymers usually are too jelly-like and lack sufficient rigidity to be used in dental floss applications, because, inter alia, they tend to break too easily upon elongation (i.e., the tensile strength at break is too high, and the elongation at break is too low for practical use). U.S. Pat. No. 5,962,572, the disclosure of which is incorporated by reference herein in its entirety, discloses oriented gels useful in a variety of applications such as low frequency vibration applications, damping of mechanical structures, and the like.

U.S. Pat. No. 5,755,243, the disclosure of which is incorporated by reference herein in its entirety, discloses a dental floss comprised of a fiber core, surrounded by an elastomeric outer layer. The outer layer provides a softer coating on a thicker floss used as a brush portion of a floss, but the floss itself is not stretchable due to the inner fiber core. A similar floss is disclosed in U.S. Pat. No. 5,875,797, the disclosure of which is incorporated by reference herein in its entirety. U.S. Pat. No. 5,918,609, the disclosure of which is incorporated by reference herein in its entirety discloses particulate modified elastomeric flosses in which particulate modification agents are either adsorbed to the surface of the floss or embedded in the surface of the floss.

U.S. Pat. No. 5,941,256, the disclosure of which is incorporated by reference herein in its entirety, discloses a dental floss having microcapsules associated with a portion of the floss that will burst and release a color to indicate use of the floss. U.S. Pat. No. 6,029,678, the disclosure of which is incorporated by reference herein in its entirety, discloses a "gel" dental floss that comprises a core material and a gel material in which the core material provides for sufficient tensile strength and the gel component provides for softness of the floss. U.S. Pat. No. 6,161,555, the disclosure of which is incorporated by reference herein in its entirety, discloses a dental floss in the form of a strand or tape made from gels having improved high tear strength and improved high tensile strength.

Accordingly, there remains a need to develop dental floss compositions that solve such problems.

SUMMARY

An elastomeric dental floss comprised of at least one elastomeric material that can be enlarged and swelled without breaking in a normal flossing operation. The dental floss provides improved and gentler application to the gums, capable of massaging the gum, more interesting and fun to use, and flexible to allow easy handling during flossing.

In one embodiment, the elastomeric dental floss comprises at least an elastomeric block copolymer, polypropylene, a plasticizer, an optional flavorant, and an optional colorant. The elastomeric dental floss preferably can be elongated up to 1,500% of its initial length without breaking, a tensile strength peak at breaking point, for a 2 mm wide sample, as measured on an Instron 4464 with $2.76 \times 10^3$ Pa (40 psig) grips, of less than 20 N·min, and an elongation at breaking point, for a 2 mm wide sample, as measured on an Instron 4464 with $2.76 \times 10^5$ Pa (40 psig) grips, of more than 100%.

In another embodiment, the elastomeric dental floss is prepared by extrusion or injection molding a mixture of at least an elastomeric block copolymer, polypropylene homopolymer, a mineral oil, an optional flavorant, and an optional colorant through a die to produce a filament dental floss product having a cross-sectional shape selected from the group consisting of circular, star-shape, trapezoidal, elliptical, square, triangular, octagonal, and rectangular.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art.

It was a surprising discovery that a gel composition may be effectively used as a dental floss. Generally, the gel composition comprises a melted blend of an elastomeric block copolymer, preferably a styrene-ethylene-butylene-styrene (SEBS) block copolymer, polypropylene homopolymer, and a plasticizer, and is a deformable and stretchable solid, that narrows as it is stretched. The gel composition may be stretched up to 3000% of its original length, and return to within 100% to 120% of its original length when relaxed. Generally, the gel composition "narrows" as it becomes stretched, and "thickens" or returns to its original diameter when relaxed. Thus, the gel composition may be stretched to be manipulated between teeth, and relaxed when contacting the gums, e.g., to clean the area.

In preferred embodiments, the elastomeric dental floss is in the form of a solid gel composition, and may be produced by extrusion methods or injection molding methods known by persons having ordinary skill in the art into filaments that also exhibit a gel like consistency, e.g., are readily deformable and stretchable, but return to their original size and shape after such deformation and stretching. It is preferred that the composition comprise an elastomeric polymeric material comprising from 80 to 99% by weight of an SEBS (styrene-ethylene/butylene-styrene) block copolymer having an unsaturated mid-block chain, from 1 to 20% by weight of a polypropylene homopolymer, from 0.01 to 5% by weight of a mineral oil. The composition may further contain from 0.001% to 1% by weight of a colorant, and from 0.05 to 1.5% of a flavorant.

Any suitable SEBS block copolymer can be used so long as it provides a final composition having the desired properties described herein. U.S. Pat. Nos. 5,334,646 and 5,508,334 disclose various SEBS copolymers having jelly-like characteristics, but the polymer described therein are not practical for use as a dental floss due to their undesirable tensile strength at break and elongation at break characteristics. The present inventors discovered that a suitable dental floss could be made by mixing from 1 to 20% by weight of a homopolymer of polypropylene with the SEBS and a plasticizing oil to provide an elastomeric composition that can be elongated up to 1,500% of its initial length without breaking, that has a tensile strength peak at breaking point, for a 2 mm wide sample, as measured on an Instron 4464 with $2.76 \times 10^5$ Pa (40 psig) grips, of less than 20 N·min, and that has an elongation at breaking point, for a 2 mm wide sample, as measured on an Instron 4464 with $2.76 \times 10^5$ Pa (40 psig) grips, of more than 100%.

Suitable block copolymers employed have the more general configuration A-B-A wherein each A is a crystalline polymer end block segment of polystyrene; and B is a elastomeric polymer center block segment of poly(ethylene-butylene). These block polymers often are referred to as SEBS block copolymers, and are readily available from a variety of commercially available sources, or can be specially designed using the guidelines provided herein, depending on the desired properties. The poly(ethylene-butylene) and polystyrene portions may be incompatible such that they can form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupts the structure, which can be restored by lowering the temperature.

The SEBS block copolymers useful in various embodiments can include a broad range of styrene end block to ethylene/butylene center block ratios of approximately 20:80 or less to 40:60 or higher Various styrene-ethylene-butylene-styrene block copolymers are commercially available from Shell Chemical Company and Pecten Chemical Company (divisions of Shell Oil Company) under trade designations Kraton G 1651, Kraton G 4600, Kraton G 4609 and the like. Other grades of (SEBS) polymers also can be utilized and include Kraton G 1855X which has a Specific Gravity of 0.92, Brookfield Viscosity of a 25 weight percent solids solution in toluene at 25° C. of 40,000 cps or 8,000 to 20,000 cps at a 20 weight percent solids solution in toluene at 25° C.

The styrene to ethylene and butylene weight ratios can vary anywhere within the following ratios 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and the like. Other ratio values of less than 19:81 or higher than 51:49 are also possible.

Other suitable block copolymers useful are those manufactured by Kuraray Co., Ltd., Tokyo, Japan, under the tradename SEPTON™. These block copolymers include, for example, styrene-ethylene/propylene-styrene block polymers (SEPS), styrene-ethylene/butylene-styrene block polymers (SEBS), styrene-ethylene-ethylene/propylene-styrene block polymers (SEEPS), and the like.

The block copolymer (either SEBS or SEPTON) preferably is admixed with from 1% to 20% by weight, more preferably from 3% to 15%, based on the total weight of the elastomeric mixture (including the plasticizer oil), of a polypropylene homopolymer. Polypropylene homopolymers are commercially available from The Dow Chemical Company, (DOW®Polypropylene 5D49, DOW®Polypropylene 5D98, DOW®Polypropylene 5E16S, DOW®Polypropylene 5E89, and the like), DuPont, GE, and others. While not intending on being bound by any theory, the inventors believe that by including a minor amount of the more rigid polypropylene homopolymer into the mixture of the elastomeric copolymer, a more suitable dental floss product can be achieved, having the desired tensile strength and elongation at break suitable for a dental floss product.

Plasticizers particularly preferred for use in practicing are known in the art, they include rubber processing oils such as paraffinic and naphthenic petroleum oils, highly refined aromatic-free paraffinic and naphthenic food and technical grade white petroleum mineral oils, isopropyl myristate, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Many such oils are known and commercially available. Examples of representative commercially oils include Amoco® polybutenes, hydrogenated polybutenes and polybutenes with epoxide functionality at one end of the polybutene polymer: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27-37 cst @ 100° F. Viscosity), L-300E (635-690 cst @ 210° F. Viscosity), Actipol E6 (365 Mn), E16 (973 Mn), E23 (1433 Mn) and the like.

Example of various commercially oils include: ARCO Prime and Tufflo oils, other white mineral oils include: Bayol, Bernol, American, Blandol, Drakeol, Ervol, Gloria, Kaydol, Litetek, Marcol, Parol, Peneteck, Primol, Protol, Sontex, and the like.

It is preferred in the various embodiments that the elastomeric copolymer is hydrogenated, and that the mid-block chain (e.g., ethylene/propylene copolymer, etc.) is unsaturated. The elastomeric copolymer, either the SEBS or other SEPTON copolymer comprises from 50% to 99% by weight of the melted blend, more preferably from 70% to 99%, more preferably from 80% to 99%, and most preferably from 85%, 90%, or 95%. The amount of styrene present in the elastomeric copolymer can range from 20% to 40% by weight of styrene, e.g., 35% to 35%, or 30%. It is preferred that the polypropylene homopolymer is included in the blend in an amount of from 1% to 20% by weight, based on the weight of the melted blend, more preferably from 2% to 15%, and most preferably, 5%, 10%, or 15%.

The overall composition, including the melted blend of polypropylene homopolymer, and elastomeric block copolymer, and the additives, preferably includes the melted blend in an amount of from 30% to 100% by weight of the melted blend, more preferably, from 75% to 99%, and most preferably more than 95%.

The elastomeric dental floss compositions may also include one or more flavoring agents. Flavoring agents that may be used include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the gel composition at a concentration of 0.01% to 5% by weight, more preferably from 0.05 to 1.5%, and more preferably, from 0.1% to 1% by weight. The gel compositions may also include one or more colors, e.g., 0.001% to 1%, and more preferably from 0.01% to 0.5% by weight of the overall composition. The elastomeric dental floss therefore may be slightly colored, or may be translucent or transparent, although a colored product is preferred.

The dental floss product described herein may further comprise additional ingredients selected from fluoride ion sources, abrasives, antiseptic or antimicrobial agents, analgesic agents, anti-inflammatory agents, L-arginine, L-arginine bicarbonate, coagulants, vitamins, and combinations thereof. In one embodiment, the dental floss compositions may optionally include fluoride, or a fluoride ion source. A wide variety of fluoride ion-yielding materials can be employed as sources of soluble fluoride in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

The elastomeric dental floss may also comprise abrasive particles, e.g., aluminium oxide, small particle silica, calcium carbonate, or other abrasive or polishing particles. The abrasive particles may assist in the removal of debris when the gel is used, e.g., as a dental floss.

The elastomeric dental floss may also comprise an antiseptic or antimicrobial selected from halogenated diphenyl ethers (e.g., triclosan, cetyl pyridinium chloride (CPC)), herbal extracts and essential oils (e.g. rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride), phenolic antiseptics, hexetidine, povidone iodine, delmopinol, salifluor, metal ions (e.g., zinc salts, for example, zinc citrate, zinc oxide, zinc lactate, and the like), sanguinarine, propolis, and combinations thereof to further aid in the beneficial effects of the basic amino acid.

In certain embodiments, the elastomeric dental floss may optionally comprise analgesic agents, anti-inflammatory agents, coagulants, vitamins, and combinations thereof.

In forming the elastomeric dental floss, the polypropylene and elastomeric copolymer preferably are blended and melted together. A plasticizer preferably is added in an amount sufficient to cause the gel to retain a solid structure, but also be deformable. The mixture then may be extruded or injection molded into sheets or strands and allowed to cool. The extruded sheets and strands may be of any diameter, and have any cross section shape (e.g., circle, square, star, rectangle, etc.). Preferably, the diameter of the extrusion is such that when the gel is stretched 150% to 1000%, and thus causing the diameter to narrow, the narrowed diameter of the gel composition may easily slide between the teeth. It is preferred that the dental floss have a diameter of from 0.5 mm to 10 mm, as measured on a circular cross-section, and more preferably from 1.0 mm to 3 mm, and most preferably 2 mm. When other cross sections are used, such as rectangular (flattened film-like materials), it is preferred that the dental floss have a width within the range of from 1 to 5 mm, more preferably from 1.5 to 3 mm, and most preferably 2 mm, and a thickness of from 1 to 5 mm, more preferably from 1.25 to 2.5 mm, and most preferably 1.5 mm. However, it will be noted that the exact diameter of the gel is not important, since the gel will continue to stretch and narrow when applied between the teeth until it reaches a sufficiently narrow diameter that allows for the gel to slide between the teeth.

The elastomeric dental floss also preferably has a basis weight within the range of from 1 to 10 gram/m, and more preferably from 1.5 to 5 g/m, and most preferably from 1.6 to 3.5 g/m. The elastomeric dental floss preferably has an apparent density of from 0.25 to 2.5 W/m, more preferably from 0.5 to 1.5 g/m, and most preferably from 0.75 to 1 g/m. The average diameter of the elastomeric dental floss before breaking preferably ranges from 0.1 to 0.75 mm, more preferably from 0.2 to 0.5 mm, and most preferably from 0.3 to 0.4 mm.

The elastomeric dental floss preferably can be stretched up to 1,500% of its original length without breaking. Using an INSTRON® apparatus, preferably and INSTRON® 4464, commercially available from Instron Corporation, Norwood, Mass., samples of the elastomeric dental floss can be tested for elongation at break and tensile strength peak at the breaking point. Preferably, the Instron apparatus is used with grips capable of holding the sample at or near $2.76 \times 10^5$ Pa (40 prig). The samples of the elastomeric dental floss used in the Instron apparatus may have a thickness of 2 mm, a width of 2 mm at the minimum center notch, with a total width of 10 mm, and a length of 29.5 mm on each side of the notch, and a notch length of 11 mm. Thus, the diameter of the relaxed specimen is 1.9 mm, which is approximately equal to the width and thickness at the center of the notch in the middle of the sample.

Using this testing procedure, the elastomeric dental floss preferably has tensile strength peak at breaking point of less than 22 N·m, more preferably less than 20 N·m, and most preferably less than 18 N·m. The elastomeric dental floss also preferably has an elongation at breaking point, for a 2 mm wide sample (at the center of the notch—i.e., at its thinnest point), of greater than 100%, more preferably greater than 150%, and most preferably greater than 200%.

The elastomeric dental floss compositions also may be coated on to a core to be used as dental floss. The core may be a fiber, which may be a multifilament fiber of polypropylene, nylon, polyester, or other polymers capable of imparting a tensile strength and/or rigidity to the floss, and may be any fiber known by those of skill in the art to be useful for forming a dental floss. Methods of manufacturing such fiber flosses are well known in the art. For example, fiber dental floss may be produced from nylon, as nylon salt is polymerized and the resulting polymer is pumped or extruded to form monofilaments. The filaments are allowed to harden, and then combined to form a strand of floss. Dental floss fibers may be produced from polytetrafluoroethylene (PTFE). The polymer is melted and extruded into thin strands. Following manufacture of the fiber floss, the fiber floss is passed through the compositions so that the fiber becomes coated. Method for coating fiber dental floss/core is also known in the art. In one embodiment, the fiber dental floss/core is treated in an emulsion bath comprising the gel compositions. The emulsion bath may optionally contain one or more waxes which adhere to the fiber floss, and thereby cause the gel composition to adhere to the core. In another embodiment, fiber floss comprising a non-PTFE fiber is coated with a first and a second coating overlaying the first coating. The first coating is a nylon bonding coating, and the second coating is a composition.

In providing a multifilament coated core, the composition and number of the filaments must be chosen. The number of filaments will be from 2 to 250 and preferably 2 to 100 depending on the denier of the filaments. The filaments may be twisted with 1 to 5 twists per inch to form the ribbon of floss. The twisting provides integrity of the floss on the spool and during subsequent handling, e.g., coating. Flavors can also be applied as a liquid or a solid. It is preferred to use a spray dried solid. Likewise, the various other additives can be applied as a liquid or a solid. When applied as a liquid the floss is dried prior to being wound onto a spool. The drying can be by radiant drying or air drying. After drying, the floss is wound onto a spool. The fibers may then be removed from the spool and coated with the gel composition.

In another aspect, the core within the gel coated core may have differing or alternative arrangements within the gel; that is to say, the core does not necessarily need to be straight, or taut when coated with the gel composition. Thus, the core may be relaxed, or formed into a "coil" shape when coated with the gel composition. Such an arrangement may be desirable to resist breakage of the dental floss, e.g., to provide two separate breaking points. Thus, for example, a core is arranged in a coil fashion and then coated with the gel composition to form a dental floss. The length of the dental floss is governed by the length of the gel composition, and when used, the gel composition and core will simultaneously elongate. In one embodiment, the tensile strength of the core is greater than the tensile strength of the gel composition, so that if the gel composition fractures under stress, the core remains intact, e.g., to floss between teeth. In another embodiment, the tensile strength of the gel composition is greater than the tensile strength of the core, so that if the core fractures under stress, the gel composition remains intact, e.g., to floss between teeth. In either of the two embodiments, although one component of the floss has broken, the other component remains intact. Such an arrangement may be desirable, as a dental floss which breaks while being used often creates discomfort on the user.

The processing conditions used to manufacture the elastomeric dental floss of the preferred embodiments will vary depending on the final properties. Preferably, a multizone single-screw extruder is used having a variety of die shapes to accommodate the different shapes to be produced (e.g., circular, rectangular, film-like, star-shaped, octagonal, etc.). The screw diameter can vary depending on the scale of product manufactured, from anywhere from 25-30 mm for lab scale, to much larger for commercial scale applications. Those having ordinary skill in the art are capable of designing a suitable extruder to manufacture the elastomeric dental floss compositions using the guidelines provided herein. A coextrusion process having a multiple layers could also be used to produce the dental floss.

Alternatively, the elastomeric dental floss products can be manufactured using an injection molding technique. Again, those having ordinary skill in the art will be capable of designing a suitable injection molding method and apparatus, using the guidelines provided herein.

The preferred embodiments now will be described in more detail with reference to the following non-limiting examples.

EXAMPLES

Elastomeric dental floss products were made and compared to commercially available dental floss products. The inventive elastomeric dental floss was prepared by melt extrusion in a multi-zone single screw MIOTTO® extruder, (Miotto Ltda, Sao Paulo, Brazil), having a screw diameter of 30 mm, an L/D ratio of 25, a compression rate of ⅓, a nominal capacity of 60 kg/hr, and a material flow rate of 12 miser. The extruder body temperatures at the various zones were (Z1=164° C.; Z2=164° C.; Z3=173; and Z4=172° C.), and the extruder head temperatures at the various zones were (Z1=175° C.; and Z2=175° C.). The product was cooled in a water cooling tank maintained at 28° C.

The elastomeric dental floss was prepared by admixing in the extruder 100% by weight, based on the total weight of the dental floss, of a polymer blend of SEBS (styrene-ethylene/propylene-styrene) block copolymer 25.8%, a propylene homopolymer 19.396%, a naphthenic mineral oil 51.7%, 0.1% of antioxidant/stabilizer component, 0.02% by weight of a colorant, and 3% by weight of mint flavoring. The elastomeric dental floss had a diameter of 1.9 mm, a basis weight of 2.45 g/m, and an apparent density of 0.83 g/m. This inventive dental floss was labeled Sample 1.

The elastomeric dental floss was compared to conventional dental floss products prepared from the following components: polyamide nylon fiber (C1), polypropylene fiber (C2), and PTFE, polytetrafluoroethylene (C3). The inventive sample was prepared to have the following dimensions: a width of 2 mm at the minimum center notch, with a total width of 10 mm, and a length of 29.5 mm on each side of the notch, and a notch length of 11 mm.

Each sample was tested on an INSTRON® 4464 tensile apparatus to measure the dimensions at break, tensile strength peak at breaking point, and elongation at breaking point. The materials were notched, as described above, to facilitate breaking. The results of the experiment are shown in Table 1 below.

TABLE 1

| PARAMETERS | Sample 1 | Current Nylon Fiber C1 | Current PP fiber C2 | Current PTFE C3 |
|---|---|---|---|---|
| Dimensions (relaxed specimen) | Ø1.9 mm | Ø~0.65 mm | Ø~0.65 mm | W 1.25 Mm T 0.06 mm |
| Basis weight | 2.45 g/m | 0.1025 g/m | 0.0765 g/m | 0.087 g/m |
| Apparent density | 0.83 g/cm | 0.94 g/cm | 0.83 g/cm | 0/85 g/cl |
| Average dimensions at maximum elongation before breaking | 0.31 mm | Minimum change | Minimum change | Minimum change |
| Tensile strength peak at breaking point (specimen 2 mm wide) | 17.6N | 55N min | 30N | 24N min |
| Elongation at breaking point (specimen 2 mm wide) | 201% | 14-20% | 21% | xx |

The results reveal that the elastomeric dental floss product prepared in Sample 1 had superior dimensions at maximum elongation before breaking, superior tensile strength peak at breaking, and superior elongation at breaking, when compared to conventional fiber dental floss products.

The invention has been described above with reference to illustrative examples, but it is to be understood that the invention is not limited to the disclosed embodiments. Alterations and modifications that would occur to one of skill in the art upon reading the specification are also within the scope of the invention, which is defined in the appended claims.

That which is claimed is:

1. An elastomeric dental floss composition comprising:
   a. a blend of an elastomeric block copolymer and polypropylene, wherein the elastomeric block copolymer comprises a styrene-ethylene/butylene-styrene block copolymer; and
   b. a plasticizer;
   wherein:
   the composition comprises from 30% to 99% by weight of the blend;
   the styrene-ethylene/butylene-styrene block copolymer comprises 20% to 40% by weight of styrene;
   the elastomeric block copolymer comprises 50% to 99% by weight of the blend;
   the propylene is a propylene homopolymer and comprises 1% to 50% by weight of the blend; and
   the dental floss can be elongated up to 1,500% of its initial length without breaking.

2. The composition of claim 1, wherein the plasticizer is a mineral oil, naphthenic oil, or a combination thereof.

3. The composition of claim 1, further comprising a flavorant, a colorant, a fluoride ion source, an abrasive, an antiseptic or antimicrobial agent, an analgesic agent, an anti-inflammatory agent, a coagulant, a vitamin, or a combination thereof.

4. The composition of claim 1, wherein the composition is in the form of a dental floss that has a tensile strength peak at breaking point, for a 2 mm wide sample, as measured on an Instron 4464 with $2.76 \times 10^5$ Pa (40 psig) grips, of less than 20 $N/m^2$.

5. The composition of claim 4, wherein the composition is in the form of a dental floss that has an elongation at breaking point, for a 2 mm wide sample, as measured on an Instron 4464 with $2.76 \times 10^5$ Pa (40 psig) grips, of more than 100%.

6. The composition of claim 1, wherein the composition is in the form of a dental floss that has a tensile strength peak at breaking point, for a 2 mm wide sample, as measured on an Instron 4464 with $2.76 \times 10^5$ Pa (40 psig) grips, of less than 18 $N/m^2$.

7. The composition of claim 6, wherein the composition is in the form of a dental floss that has an elongation at breaking point, for a 2 mm wide sample, as measured on an Instron 4464 with $2.76 \times 10^5$ Pa (40 psig) grips, of more than 200%.

8. The composition of claim 7, wherein the composition is in the form of a dental floss that has an average diameter at maximum elongation before breaking, for a 2 mm wide sample, as measured on an Instron 4464 with $2.76 \times 10^5$ Pa (40 psig) grips, of less than 0.35 mm.

9. An elastomeric dental floss composition according to claim 1, wherein: the elastomeric block copolymer is a styrene-ethylene/butylene styrene block copolymer; the polypropylene is a propylene homopolymer; and the plasticizer is a naphthenic mineral oil.

10. The composition of claim 8, wherein the plasticizer is a mineral oil, naphthenic oil, or a combination thereof.

* * * * *